United States Patent [19]

Manecke et al.

[11] Patent Number: 4,546,078
[45] Date of Patent: Oct. 8, 1985

[54] POLYMER CONTAINING BIOCATALYST

[75] Inventors: Georg Manecke; Udo Klussmann, both of Berlin, Fed. Rep. of Germany

[73] Assignee: Schering Aktiengesellschaft, Berlin, Fed. Rep. of Germany

[21] Appl. No.: 550,159

[22] Filed: Nov. 9, 1983

[30] Foreign Application Priority Data

Nov. 9, 1982 [DE] Fed. Rep. of Germany ....... 3241829

[51] Int. Cl.⁴ ................... C12P 33/00; C12N 11/08
[52] U.S. Cl. .................................. 435/52; 435/56; 435/59; 435/60; 435/61; 435/180; 435/181; 435/182
[58] Field of Search .............. 435/180, 181, 182, 60, 435/52, 56, 59, 61

[56] References Cited

U.S. PATENT DOCUMENTS 4,352,884 10/1982 Nakashima et al. ............... 435/180
4,421,855 12/1983 Watanabe et al. .................. 435/180

Primary Examiner—Sam Rosen
Attorney, Agent, or Firm—Millen & White

[57] ABSTRACT

A biocatalyst contains microorganisms, e.g., of the species *Arthrobacter simplex, Aspergillus ochraceus, Bacillus sphaericus, Curvularia lunata, Flavobacterium dehydrogenans, Mycobacterium spec.*, or *Saccharaomyces uvarum,* immobilized on a copolymer of acrolein and 1-vinyl-2-pyrrolidone, crosslinked by reaction with an alkylenedioxydiamine of the formula $$H_2NO-(CH_2)_nONH_2$$

wherein n is a number of 2 to 12. The preparation of steroids is also disclosed.

19 Claims, No Drawings

POLYMER CONTAINING BIOCATALYST

BACKGROUND OF THE INVENTION

This invention relates to a new biocatalyst, a process for its preparation, and the use thereof for the microbiological conversion of steroids.

As is known, microorganism cultures are frequently utilized for steroidal conversions. Cultures of the species *Arthrobacter simplex*, ATCC 6946, 13260, and IFO 3530, or *Bacillus sphaericus*, ATCC 7054, 7055, 12488, and 13805, can be used for the $\Delta^1$-dehydrogenation of 3-keto-$\Delta^4$-steroids. Cultures of *Flavobacterium dehydrogenans*, ATCC 13930 are used, inter alia, for converting 3$\beta$-hydroxy-$\Delta^5$-steroids into 3-keto-$\Delta^4$-steroids. Suitable for the reduction of keto steroids are, for example, cultures of *Saccharomyces uvarum* (NCYC 91 or CBS 1508). Futhermore, worth mentioning is the side chain degradation of steroids which can be performed, inter alia, with cultures of *Mycobacterium spec*. (NRRL-B 3683 and NRRL-B 3805). Also, the 11$\alpha$- and 11$\beta$-hydroxylation of steroids can be mentioned, e.g., using cultures of the species *Aspergillus ochraceus* (CBS 13252, ATCC 1008, ATCC 12337, ATCC 18500, or NRRL 405) and, respectively, with *Curvularia lunata* (NRRL 2380, NRRL 2434, ATCC 12017, or IFO 6286).

SUMMARY OF THE INVENTION

It is an object of this invention to provide a new catalytic form of microorganisms such as those useful in steroidal conversions, e.g., those mentioned above.

These objects have been attained by providing new biocatalysts, containing immobilized microorganisms, e.g., those of the species *Arthrobacter simplex, Aspergillus ochraceus, Bacillus sphaericus, Curvularia lunata, Flavobacterium dehydrogenans, Mycobacterium spec.,* or *Saccharomyces uvarum,* wherein the microorganisms are immobilized on a copolymer of acrolein and 1-vinyl-2-pyrrolidone, crosslinked by reaction with an alkylenedioxydiamine of the formula

$$H_2NO\text{---}(CH_2)_n ONH_2$$

wherein n is a number from 2 to 12. The biocatalyst generally contains 10–75 percent by weight of microorganisms and has a particle size of 0.05–1 mm.

DETAILED DISCUSSION

Using the process of this invention, biocatalysts can be produced, e.g., from the above-mentioned microorganisms wherein the microorganisms are present in an immobilized but propagable form. The biocatalysts of this invetion are distinguished by superior effectiveness compared with other biocatalysts having microorganisms fixed in polymers.

The microorganisms used to prepare the biocatalysts are incubated in fully conventional fashion. After the incubation has been completed, they are conventionally filtered off or removed by centrifuging, conventionally washed with water or dilute buffer solution and again conventionally filtered or centrifuged. The thus-obtained moist biomass can be used without further processing for the preparation of the biocatalyst, using an amount of moist biomass approximately 0.5 to 7 times the amount of the acrolein-(1-vinyl-2-pyrrolidone) copolymer (dry mass). On the other hand, the biomass can also be dried by spray-drying, in which case the amount of dry powder utilized is 0.1 to 2 times as much as the amount of copolymer (dry mass). The precise amount used is selected generally to achieve a 10–75 percent of weight loading of the polymer with microorganisms.

The acrolein-(1-vinyl-2-pyrrolidone) copolymer employed in the biocatalyst can be prepared by polymerizing acrolein and 1-vinyl-2-pyrrolidone in an aqueous solution in the presence of an initiator at 10°–40° C. In this process, peroxides are preferably used as the initiators, e.g., hydrogen peroxide, benzoyl peroxide, cumene hydroperoxide, di-tert-butyl peroxide, or especially potassium peroxydisulfate. The process is conducted at a temperature of 10°–40° C., typically for times of 4–48 hours, and particularly at a temperature of 15°–30° C. The reaction can be conducted trouble-free at room temperature. Normal polymerization techniques are used.

The copolymer, essentially independently of the number of moles of acrolein employed per mole of 1-vinyl-2-pyrrolidone, is composed of approximately equixolar quantities of both components. This can be proven by conventional determination of aldehyde groups and elementary analysis. However, to obtain satisfactory yields of copolymer, it is expedient to use about 0.5–1.5 moles, preferably 0.5–1.0 mole, of acrolein per mole of 1-vinyl-2-pyrrolidone. Suitably, polymerization is conducted in an aqueous solution containing 2–20% of the acrolein-(1-vinyl-2-pyrrolidone) mixture. Preferably, 0.5–10 mole percent and especially 1–4 mole percent of the initiator is employed per mole of acrolein-(1-vinyl-2-pyrrolidone) mixture. After polymerization has been completed, the monomers and initiator are removed, preferably by dialysis, and the resultant solution of the copolymer can be directly employed for preparing the biocatalyst. On the other hand, it is also possible, of course, to dilute the copolymer solution prior to use or, alternatively, to concentrate it, for example, by freeze-drying.

The alkylenedioxydiamines are known and can be produced by conventional methods (J. Chem. Soc. 1947 : 963 et seq.). Among the alkylenedioxydiamines, those are especially preferred which contain 5–9 carbon atoms. Since the longer-chain alkylenedioxydiamines are only sparingly soluble in water, it is advantageous to use their salts (e.g., the monochlorides or monosulfates) for preparing the biocatalysts.

To produce the biocatalyst, the microorganisms can be suspended in the acrolein-(1-vinyl-2-pyrrolidone) copolymer solution. It is also possible to add up to 25 percent of an inert solvent—e.g., dimethylformamide or dimethyl sulfoxide. Once a uniform suspension has been created, an amount of alkylenedioxydiamine is added under agitation such that the molar ratio of oxyamino groups in the crosslinking agent and of aldehyde groups in the copolymer is preferably 0.5 to 1.5, but especially 1:1. The preparation is conducted at a temperature of 0°–40° C. After the pH drops, the mixture is adjusted to pH 3–7 with a buffer solution or with an alkaline solution. After 0.5–12 hours, the biocatalyst is separated and comminuted. It is advantageous to screen the biocatalyst in the wet state and to utilize the screen fractions from 0.02 to 2 mm, preferably those from 0.05 to 1.5 mm, most preferably 0.05 to 1.0 mm particle size, for use in conversion of steroids.

Aqueous suspensions of the biocatalyst can be utilized to catalyze steroid transformations in the same way as the corresponding suspensions of the microorganisms proper. Thus, first of all, the most favorable fermentation conditions are determined by means of the customary routine preliminary tests, e.g., substrate concentration and technical conditions such as temperature, aeration, pH value, and the optimum fermentation period.

In a preferred embodiment, micronized steroid is added to the suspension of the biocatalyst, fermentation is performed, and, after the conversion has been achieved, the finely dispersed product is separated by screening from the coarse-grained biocatalyst. The latter can then be reused for other steroid transformations—optionally after reactivation by treatment with a nutrient solution. In an especially preferred embodiment, the steroid is added in the form of a solution or in micronized form to the suspension of the biocatalyst. The reaction mixture is incubated at a temperature of 20°–40° C. until the steroid has been converted. Thereafter, the biocatalyst is separated from the aqueous suspension of the thus-formed steroid by means of a screen (sieve).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The following practical examples serve to explain the process of this invention for the preparation of the biocatalyst and the use of the process for steroid transformations.

EXAMPLE 1

(a) Two 2-liter Erlenmeyer flasks, each containing 500 ml of a sterilized nutrient solution of 0.5% corn steep, 0.1% yeast extract, and 0.05% glucose, adjusted to pH 7.0, are inoculated each with a lyophilized culture of Arthrobacter simplex (ATCC 6946) and shaken on a rotary shaker for 48 hours at 30° C. This subculture serves for inoculation of a 50-liter glass fermentor filled with 30 l of a sterilized medium of 0.5% corn steep, 0.1% yeast extract, and 0.05% glucose, adjusted to pH 7.0. After inoculation, germination is conducted for 24 hours at 29° C. under aeration (10 liters per minute), 0.7 atm. gauge pressure, and agitation (220 rpm). A steel fermentor is then inoculated with this preliminary fermentation culture; this steel fermentor contains 500 l of a medium, sterilized at 121° C. and 1.1 atm. gauge, made up of 0.5% corn steep, 0.1% yeast extract, and 0.05% glucose, adjusted to pH 7.0. Under the conditions of the preliminary fermentor, germination is likewise carried out for 24 hours to optimum cell density.

Subsequently, the culture is separated in a laboratory separator LG 205 [company: Westfalia Separator AG, Oelde (Westphalia)] at 10,000 rpm. The thus-centrifuged cell material is washed with distilled water to remove any adhering components of the nutrient medium and again centrifuged.

The moist bacterial paste (2.85 kg) produced in this way is made into a slurry in 2.85 l of a 0.05-molar tris(-hydroxymethyl)methylamine buffer of pH 7.6, forced through a metallic gauze filter to divide cellular clumps, and spray-dried in a universal laboratory spray dryer [company: Zahn and Co., Hameln, W. Germany] at a vaporization temperature of 80° C.; the feed is 600 ml of cell suspension per hour.

In this way, 513 g of Arthrobacter simplex dry powder is obtained.

(b) Under nitrogen, 44.9 g of re-distilled acrolein and 133.4 g of re-distilled 1-vinyl-2-pyrrolidone are dissolved in one liter of water, combined with 10.8 g of potassium peroxodisulfate, stirred until the salt has been dissolved, and then allowed to stand at room temperature for 24 hours.

The reaction mixture is then dialyzed for 3 days against distilled water, thus obtaining the acrolein-(1-vinyl-2-pyrrolidone) copolymer solution, containing 43.5 mg of copolymer per ml of solution. The content of aldehyde groups in the copolymer is 5.32 millimoles per gram.

(c) 228 ml of the acrolein-(1-vinyl-2-pyrrolidone) copolymer solution (containing 10 g of copolymer) is combined with 22 ml of dimethylformamide. Then, under vigorous agitation, 10 g of Arthrobacter simplex dry powder is added to the solution and, after this powder has been uniformly distributed, 5.32 ml of a 0.5-molar aqueous solution of 1,6-bis(aminooxy)hexane, monohydrochloride, is added thereto. As soon as the pH drops, it is adjusted to pH 4.5 by adding 1N sodium hydroxide solution. After 10 minutes, the reaction mixture is filled up to 2.5 l with 0.05-molar phosphate buffer (pH 6.86), stirred for another hour, the resultant product is comminuted, washed with the phosphate buffer, and screened in the wet state. The screen fractions having a particle size of 0.1–0.5 mm are stored in the moist condition and utilized for steroid transformation. The moist biocatalyst contains 14% dry mass.

(d) A suspension is prepared from 440 mg of the moist biocatalyst and 50 ml of 0.05-molar phosphate buffer, pH 6.86, combined with 180 mg of micronized hydrocortisone, and shaken at room temperature for 24 hours. The biocatalyst is then removed by filtration, and the content of thus-formed prednisolone is determined by differential pulse polarography. The yield is 87% of theory.

The filtered-off biocatalyst can be reused for hydrocortisone conversion.

EXAMPLE 2

(a) 106.4 g of 1,8-dibromooctane is dissolved in 400 ml of absolute ethanol, combined with 82.2 g of hydroxycarbamic acid ethyl ester and 43.8 g of potassium hydroxide, and heated under reflux for 6 hours. The reaction mixture is concentrated under vacuum, the residue is diluted with water, extracted with diethyl ether, and the ether extract is concentrated.

The thus-obtained residue is combined with a solution of 40 g of potassium hydroxide in 80 ml of water and heated under reflux for 2.5 hours.

The reaction mixture is allowed to cool, extracted with diethyl ether, and the organic phase is fractionated, thus obtaining 16.43 g of 1,8-diaminooxyoctane, bp 115° C./0.4 torr.

Under agitation, 16.43 g of diaminooxyoctane is combined with 167.3 ml of 1N aqueous hydrochloric acid until the pH of the solution is 2.4. The solution is then concentrated under vacuum and the residue recrystallized from 93% strength ethanol, thus obtaining 14.83 g of diaminooxyoctane monohydrochloride, mp 174° C.

(b) Under the conditions of Example 1(c)—but using the corresponding quantity of 1,8-diaminooxyoctane, monohydrochloride, an Arthrobacter simplex (ATCC 6946) biocatalyst is prepared, which likewise has the capability of dehydrogenating hydrocortisone to prednisolone.

EXAMPLE 3

(a) Under the conditions of Example 1(a), but using a nutrient medium containing 0.5% corn steep liquor, 0.3% yeast extract, and 0.2% glucose, 500 l of a *Flavobacterium dehydrogenans* (ATCC 13930) culture is produced and processed to 731 g of *Flavobacterium dehydrogenans* dry powder.

(b) Under the conditions of Example 1(c), but using the dry powder of *Flavobacterium dehydrogenans*, a biocatalyst is prepared having the capability of converting 3β,17α,21-trihydroxy-5-pregnen-20-one into 17α,21-dihydroxy-4-pregnene-3,20-dione.

EXAMPLE 4

(a) A 2-liter Erlenmeyer flask containing 500 ml of a sterilized nutrient medium, consisting of 2% edamine, 5% dextrose, and 0.3% corn steep liquor, pH 5.3, is inoculated with a lyophilized culture of *Saccharomyces uvarum* (NCYC 91) and shaken for 24 hours at 26° C. on a rotary shaker.

This subculture is used to inoculate a 20-liter glass fermentor with 15 l of sterile culture medium (2% edamine, 5% dextrose, and 0.3% corn steep liquor, pH 5.3), and germination is carried out at 26° C. under aeration with sterile air, 0.7 atm. gauge pressure, and agitation for 60 hours.

Thereafter the culture broth is centrifuged in a laboratory separator, and the cell sediment, to remove components of the medium, is washed with 3 l of distilled water and again centrifuged. The cell material prepared in this way is made into a slurry with 0.05-molar phosphate buffer according to Sörensen, pH 6.4, and spray-dried in a laboratory spray-dryer at 80° C. After termination of spray-drying, 195 g of dry yeast powder is collected in the receiver.

(b) Under the conditions of Example 1(c), but using the dry yeast powder, a biocatalyst is prepared having the capability of reducing 4-androstene-3,17-dione to 17β-hydroxy-4-androstene-3-one.

EXAMPLE 5

(a) A 750-milliliter Erlenmeyer flask is charged with 200 ml of a sterile nutrient solution, containing 1% yeast extract, 0.45% disodium hydrogen phosphate, 0.34% potassium dihydrogen phosphate, and 0.2% "Tagat" 02—adjusted to pH 6.7—then inoculated with a supernatant broth of a dry culture of Mycobacterium spec. NRRL-B 3805, and shaken for 3 days at 30° C. at 190 rpm.

A 50-liter fermentor filled with 40 l of a sterile nutrient solution containing 1.23% yeast extract (65% strength), 0.68% potassium dihydrogen phosphate, and 0.2% "Tagat" 02—adjusted to pH 0.6—is inoculated with 200 ml of the Mycobacterium spec. germination culture, and the subculture is incubated at 30° C. under aeration (2 m³ per hour) for 48 hours. The bacterial mass is removed by centrifuging, made into a slimy broth with water, and again centrifuged.

(b) Under the conditions of Example 1(c), but with the use of 25 g of Mycobacterium spec. bacterial mass, a biocatalyst is prepared having the capability of transforming 4-cholesten-3-one into 4-androstene-3,27-dione.

EXAMPLE 6

(a) A wort culture slant with *Curvularia lunata* (NRRL 2380), age 7-14 days, is floated off with 3 ml of physiological sodium chloride solution and used for inoculating a 2-liter Erlenmeyer flask containing 500 ml of a nutrient solution, sterilized in an autoclave for 30 minutes at 120° C., made up of 2% glucose and 2% corn steep, adjusted to pH 6.5. After 60 hours of shaking on a rotary shaker at 30° C., 250 ml of this incubation culture serves for inoculation of the preliminary fermentor. A 20-liter preliminary fermentor, charged with 15 l of a nutrient medium having the same composition as the incubating medium and sterilized at 121° C. and 1 bar gauge pressure, is inoculated with 250 ml of the germination culture. With the addition of silicone SH as the defrother, germination is then conducted to 29° C. and 0.6 bar pressure under aeration (15 liters/minute) and agitation (220 rpm) for 24 hours.

The fungal mycelium is thereafter suctioned off, made into a slimy broth with water, and again suctioned off.

(b) Under the conditions of Example 1(c), but using 25 g of *Curvularia lunata* fungal mycelium, a biocatalyst is produced suitable for converting 17α,21-dihydroxy-4-pregnene-3,20-dione into hydrocortisone.

EXAMPLE 7

(a) A 2-liter Erlenmeyer flask with 500 ml of a sterile nutrient solution containing 1% corn steep liquor, 1.25% soybean meal, and 0.005% soybean oil is inoculated with a 10-day-old agar slant of *Aspergillus ochraceus*, ATCC 1008, and shaken for 72 hours at 30° C. and at 165 rpm.

This incubation culture is used for inoculating a 20-liter glass fermentor—containing 14.5 l of a sterilized nutrient solution having the same composition—and germination is conducted under agitation (220 rpm) and aeration (15 liters per minute) at 30° C.

After 24 hours of growth phase, the mycelium is suctioned off, made into a slimy broth with water, and again suctioned off.

(b) Under the conditions of Example 1(c), but using 25 g of *Aspergillus ochraceus* fungal mycelium, a biocatalyst is prepared usable for converting 17α,21-dihydroxy-4-pregnene-3,20-dione into 11α,17α,21-trihydroxy-4-pregnene-3,20-dione.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A biocatalyst comprising an effective amount of a microorganism which is of the species *Arthrobacter simplex, Aspergillus ochraceus, Bacillus sphaericus, Curvularia lunata, Flavobacterium dehydrogenans, Mycobacterium spec.,* or *Saccharomyces uvarum,* and which is immobilized on a copolymer of acrolein and 1-vinyl-2-pyrrolidone which is crosslinked by reaction with an alkylenedioxydiamine of the formula

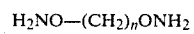

wherein n is a number of 2–12.

2. A biocatalyst of claim 1, wherein the amount of microorganism is 10–75 percent by weight.

3. A biocatalyst of claim 1, having a particle size of 0.02 to 2 mm.

4. A biocatalyst of claim 1, having a particle size of 0.05 to 1 mm.

5. A biocatalyst of claim 1, wherein the proportion of comonomeric components in the copolymer is 0.5 to 1.5 moles of acrolein per mole of 1-vinyl-2-pyrrolidone.

6. A biocatalyst of claim 1, wherein the proportion of comonomeric components in the copolymer is 0.5 to 1.0 mole of acrolein per mole of 1-vinyl-2-pyrrolidone.

7. A biocatalyst of claim 1, wherein n is 5 to 9.

8. A biocatalyst of claim 5, wherein the amount of crosslinking agent is such that the molar ratio of oxyamino groups to the aldehyde groups of the copolymer is 0.5 to 1.5.

9. In a biocatalyst comprising a microorganism immobilized on a polymeric substrate, the improvement wherein the polymeric substrate is a copolymer of acrolein and 1-vinyl-pyrrolidone which is crosslinked by reaction with an alkylenedioxydiamine of the formula

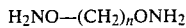
$H_2NO-(CH_2)_nONH_2$ wherein n is a number of 2 to 12.

10. A process for the preparation of a biocatalyst of claim 1, comprising combining a suspension of the microorganism in an aqueous solution of the copolymer with the alkylenedioxydiamine.

11. A process for the preparation of a biocatalyst according to claim 10, which is conducted at a temperature of 0°–40° C.

12. A process for the preparation of a biocatalyst according to claim 10, further comprising preparing the copolymer by polymerizing acrolein and 1-vinyl-2-pyrrolidone in an aqueous solution in the presence of an initiator at 10°–40° C.

13. A process for the preparation of a biocatalyst according to claim 12, wherein 0.5–1.0 mole of acrolein per mole of 1-vinyl-2-pyrrolidone is used in the polymerization.

14. A process for the preparation of a biocatalyst according to claim 10, wherein the ratio of oxyamino groups of the alkylenedioxydiamine to the aldehyde groups of the copolymer is 0.5 to 1.5.

15. A biocatalyst prepared by the process of claim 10.

16. In the microbiological conversion of a steroid using a biocatalyst comprising a microorganism suspended on a substrate, the improvement wherein the biocatalyst is that of claim 1.

17. In the microbiological conversion of a steroid using a biocatalyst comprising a microorganism suspended on a substrate, the improvement wherein the biocatalyst is that of claim 9.

18. A microbiological conversion of claim 16, wherein the biocatalyst is used in aqueous suspension.

19. A microbiological conversion of claim 18, comprising adding a steroid in the form of a solution or in micronized form to the aqueous suspension of the biocatalyst; incubating the reaction mixture at a temperature of 20°–40° C. until the steroid has been converted; and thereafter separating the biocatalyst from the aqueous suspension of the thus-formed steroid.

* * * * *